US012690884B2

(12) United States Patent (10) Patent No.: US 12,690,884 B2

Fujimagari et al. (45) Date of Patent: Jul. 28, 2026

(54) DEVICE SUPPORT, MEDICAL DEVICE, AND TREATMENT METHOD

(71) Applicant: TERUMO KABUSHIKI KAISHA, Tokyo (JP)

(72) Inventors: Hideki Fujimagari, Fujinomiya-city (JP); Yasushi Kinoshita, Fujinomiya-city (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 161 days.

(21) Appl. No.: 18/610,447

(22) Filed: Mar. 20, 2024

(65) Prior Publication Data

US 2024/0325043 A1 Oct. 3, 2024

(30) Foreign Application Priority Data

Mar. 27, 2023 (JP) ................................. 2023-050103

(51) Int. Cl.
*A61B 17/3207* (2006.01)
*A61B 17/00* (2006.01)

(52) U.S. Cl.
CPC ................ *A61B 17/320758* (2013.01); *A61B 17/00234* (2013.01); *A61B 2017/00017* (2013.01); *A61B 2017/00238* (2013.01); *A61B 2017/00314* (2013.01); *A61B 2017/00778* (2013.01); *A61B 2017/00991* (2013.01); *A61B 2217/005* (2013.01)

(58) Field of Classification Search
CPC ...... A61B 17/320758; A61B 17/00234; A61B 17/32002; A61B 17/320725; A61B 17/32075; A61B 17/320783
See application file for complete search history.

(56) References Cited

U.S. PATENT DOCUMENTS

| | | | | |
|---|---|---|---|---|
| 5,882,329 A * | 3/1999 | Patterson | ........... | A61B 17/3207 604/523 |
| 2002/0161384 A1* | 10/2002 | Wulfman | ....... | A61B 17/320758 606/159 |
| 2005/0004553 A1* | 1/2005 | Douk | ................ | A61M 25/0021 604/523 |
| 2020/0155194 A1* | 5/2020 | Schneider | ...... | A61B 17/320758 |
| 2021/0052294 A1* | 2/2021 | Fleming | ........... | A61B 17/32053 |
| 2022/0240975 A1 | 8/2022 | Flury et al. | | |

* cited by examiner

*Primary Examiner* — Tuan V Nguyen
(74) *Attorney, Agent, or Firm* — Buchanan Ingersoll & Rooney PC

(57) ABSTRACT

A device support insertable into a sheath, the device support supporting a medical device including a rotatable drive shaft extending from a distal end to a proximal end, and an operation unit that accommodates a drive source connected to the drive shaft, the device support including a plurality of tubular bodies that accommodates the drive shaft and an outer tube, in which a first tubular body disposed on a most proximal end side among the plurality of tubular bodies has a proximal end connection portion connectable to the operation unit at a proximal end portion of the first tubular body, and the plurality of tubular bodies includes at least a second tubular body and a third tubular body having an outer diameter smaller than an inner diameter of the second tubular body, and the second tubular body and the third tubular body are movable relative to one another.

5 Claims, 9 Drawing Sheets

DEVICE SUPPORT, MEDICAL DEVICE, AND TREATMENT METHOD

CROSS-REFERENCES TO RELATED APPLICATIONS

This application claims priority to Japanese Application No. 2023-050103 filed on Mar. 27, 2023, the entire content of which is incorporated herein by reference.

TECHNOLOGICAL FIELD

The present disclosure generally relates to a device support used for supporting a medical device to be inserted into a body lumen, a medical device, and a treatment method.

BACKGROUND DISCUSSION

In a case where a thrombus, a plaque, a calcified lesion, or the like occurs in the body lumen, it can be necessary to quickly remove the thrombus, the plaque, the calcified lesion, or the like. For example, U.S. Patent Application Publication No. 2022/0240975 describes a device for removing a thrombus. This device includes a hub in which a drive source that applies a rotational force is disposed and that is operated by an operator, a drive shaft that is rotationally driven by the drive source, an outer tube that rotatably accommodates the drive shaft, and a cutting section that is fixed to a distal end of the drive shaft and is capable of cutting a thrombus.

In the device described in U.S. Patent Application Publication No. 2022/0240975, the drive shaft is movable in an axial direction inside the hollow outer tube (see FIG. 4B of U.S. Patent Application Publication No. 2022/0240975). Therefore, when the cutting section fixed to the distal end of the drive shaft comes into contact with the thrombus, the drive shaft moves to a side of the distal end and a length of the drive shaft exposed from the outer tube increases. For this reason, since a range of the drive shaft not supported by the outer tube is increased and the drive shaft is rather easily bent, it can be difficult to transmit a force in a distal end direction, and the ability to cut the thrombus is deteriorated.

Therefore, the outer tube covering the drive shaft can be fixed to the hub, and the drive shaft and the outer tube can be integrally moved in the axial direction. In this case, even if the cutting section comes into contact with the thrombus, since a portion up to the distal end portion close to the cutting section of the drive shaft is always covered and supported by the outer tube, the drive shaft is hardly bent and rather easily transmits the force in the distal end direction.

However, when the hub is moved, the drive shaft and the outer tube are simultaneously moved in the axial direction, so that the drive shaft and the outer tube can be easily curved (or bent) and rather easily damaged.

SUMMARY

A device support, a medical device, and a treatment method are disclosed that are capable of suppressing damage of a rotatable drive shaft of a medical device and other long devices used together with the drive shaft.

(1) A device support according to the present disclosure, which is insertable into a sheath, the device support supporting a medical device including a rotatable drive shaft extending from a distal end to a proximal end, and an operation unit that accommodates a drive source connected to the drive shaft, the device support including a plurality of tubular bodies that accommodates the drive shaft, in which a first tubular body disposed on a most proximal end side among the plurality of tubular bodies has a proximal end connection portion connectable to the operation unit at a proximal end portion of the first tubular body, and the plurality of tubular bodies includes at least a second tubular body and a third tubular body having an outer diameter smaller than an inner diameter of the second tubular body, and the second tubular body and the third tubular body are movable relative to one another.

In the device support according to (1), while the medical device moves in an axial direction with respect to the sheath into which the drive shaft of the medical device is inserted, the plurality of tubular bodies can suppress the curvature of the rotatable drive shaft of the medical device, smoothly maintain the rotation of the drive shaft, and can suppress the damage of the drive shaft. Furthermore, the plurality of tubular bodies is relatively movable such that the device support inserts only a distal end portion of the device support into the sheath while the medical device is inserted into the sheath to the vicinity of the proximal end portion. Therefore, the device support can suppress the curvature of the rotatable drive shaft to smoothly maintain the rotation of the drive shaft and can suppress the sheath from being deformed due to excessive insertion of the device support into the sheath. Therefore, the device support can suppress damage to the drive shaft and other long devices used together with the drive shaft such as a sheath.

(2) In the device support according to (1) described above, the second tubular body may be nested and disposed coaxially to the second tubular body. As a result, the second tubular body and the third tubular body can expand and contract in the axial direction, and can cover the medical device with lumens of the second tubular body and the third tubular body to effectively suppress the curvature of the drive shaft of the medical device.

(3) Another aspect of a device support according to the present disclosure is a device support supporting a medical device including a rotatable drive shaft extending from a distal end to a proximal end, an outer tube that rotatably accommodates the drive shaft, and an operation unit that accommodates a drive source connected to the drive shaft, the device support including: an expandable portion formed to be long from the distal end to the proximal end and expandable/contractible in an axial direction that is a long direction; and a proximal end connection portion disposed at a proximal end portion of the expandable portion and connectable to the outer tube and/or the operation unit, in which the expandable portion includes at least two support portions in which a support hole penetrating in the axial direction is formed, and at least two of the support portions are disposed side by side in the axial direction.

In the device support according to (3) described above, while the medical device moves in the axial direction with respect to the drive shaft of the medical device and the sheath into which the outer tube is inserted, the expandable portion including the support portions can suppress the curvature of the rotatable drive shaft of the medical device and the outer tube that rotatably accommodates the drive shaft, and can smoothly maintain the rotation of the drive shaft. Furthermore, the expandable portion of the device support is expandable/contractible such that the device support inserts only a distal end portion of the device support into the sheath while the medical device is inserted into the sheath to the vicinity of the proximal end portion. Therefore, the device support can suppress the curvature of the rotatable drive shaft of the medical device and the outer tube that rotatably accommodates the drive shaft to smoothly maintain the rotation of the drive shaft and can suppress the sheath from being deformed due to excessive insertion of the device support into the sheath. Therefore, the device support can suppress damage to the drive shaft and damage to other elongated devices used together with the drive shaft such as the outer tube and the sheath.

(4) In the device support according to (3) described above, a slit extending from a distal end to a proximal end may be formed in each of the support portions, and the support portion may be discontinuous by the slit in a circumferential direction that is a direction surrounding the support hole. This allows the device support to receive the outer tube and the drive shaft into the support hole from the side intersecting the axial direction of the support portion. Therefore, it is not necessary to cover the medical device with the device support in advance before inserting the medical device into the sheath, and workability can be improved. Thus, for example, even with the drive shaft and the outer tube of the medical device inserted in the sheath, the device support can be attached to the medical device so as to accommodate the outer tube and the drive shaft in the support hole.

(5) In the device support according to (3) or (4) described above, the expandable portion may include a tubular distal end connection portion in which a distal end through-hole penetrating in the axial direction is formed at a distal end portion, and an outer diameter of at least a part of an outer peripheral surface of the distal end connection portion may decrease in a tapered shape toward a distal end so as to form a convex curved surface in a cross section in which an axial center is located. As a result, the distal end connection portion of the device support can be inserted into a proximal end opening of the sheath, and the device support can be smoothly connected to the sheath without damaging the sheath.

(6) In the device support according to (1) or (2) described above, third tubular body disposed on a most distal end side among the plurality of tubular bodies may include: a distal end connection portion disposed at a distal end portion of the third tubular body and insertable into the sheath; and an insertion restriction portion disposed on a proximal end side with respect to the distal end connection portion and restricting insertion of the third tubular body into the sheath. As a result, it is possible to prevent the third tubular body disposed on the most distal end side from moving to the distal end side from an appropriate position.

(7) In the device support according to (6) described above, the insertion restriction portion may protrude radially outward from an outer peripheral surface of the third tubular body disposed on the most distal end side among the plurality of tubular bodies. As a result, the insertion restriction portion of the third tubular body disposed on the most distal end side can prevent the third tubular body from moving to the distal end side from an appropriate position.

(8) In the device support according to (1) or (2) described above, a flexible portion having partially low flexural rigidity in an axial direction may be formed in the third tubular body disposed on a most distal end side among the plurality of tubular bodies. As a result, in the device support, a portion excluding the flexible portion becomes linear, and only the flexible portion can be curved, as necessary. Therefore, even in a case where it is difficult to dispose the operation unit straight on an extension line in a proximal direction from the proximal end portion of the sheath, it is possible to support the outer tube and the drive shaft so as not to bend more than necessary by making most of the device support linear and bending only the flexible portion.

(9) In the device support according to (8) described above, the flexible portion may be an opening penetrating from an outer peripheral surface to an inner peripheral surface, the outer peripheral surface extending in a circumferential direction of the third tubular body disposed on the most distal end side. Thus, the flexible portion can be easily formed on the third tubular body.

(10) In the device support according to any one of (1) to (9) described above, when the operation unit to which the drive shaft, the outer tube, and the device support are connected is moved to a distal end side in a state where a distal end portion of the device support is fixed to the sheath, the distal end portion of the device support fixed to the sheath does not move, and the drive shaft and the outer tube may be movable to the distal end side. As a result, the device support can suppress the curvature of the drive shaft and the outer tube that move with the movement of the operation unit and can smoothly maintain the rotation of the drive shaft.

(11) A medical device according to the present disclosure can be a medical device including: a rotatable drive shaft that extends from a distal end to a proximal end; an operation unit that accommodates a drive source connectable to the drive shaft; and an outer tube that rotatably accommodates the drive shaft, in which the operation unit includes a connection portion connectable to the outer tube.

In the medical device according to (11) described above, since the outer tube can be connected to the operation unit, the outer tube can be connected to the operation unit to integrally move the drive shaft and the outer tube when the drive shaft is rotated. For this reason, it is possible to prevent the outer tube from being damaged by interference of the rotating drive shaft and/or a member rotated by the drive shaft with the outer tube.

(12) In the medical device according to (11) described above, the outer tube includes a suction port communicating with a lumen of the outer tube. As a result, a suction force received from the suction port is applied to the lumen of the outer tube, and an object in the body can be sucked and removed by the outer tube.

(13) The medical device according to (11) or (12) described above may further include a device support that includes an expandable portion formed to be long from the distal end to the proximal end and expandable/contractible in an axial direction that is a long direction, and a proximal end connection portion disposed at a proximal end portion of the expandable portion, in which the operation unit may be connectable to the proximal end connection portion of the device support. As a result, since the proximal end connection portion of the device support can be moved together with the operation unit, operability is improved.

(14) In the medical device according to (13) described above, a distal end of the outer tube and a distal end of the device support are relatively movable in an axial direction in a state where the operation unit, the outer tube, and the device support are connected. This may cause the expandable portion of the device support to expand and contract such that only the distal end portion of the device support is inserted into the sheath while the drive shaft and the outer tube are inserted into the sheath.

(15) A treatment method according to the present disclosure can include: conveying a wire device including a wire through a guiding catheter to a target position of a blood vessel; conveying a rotatable drive shaft in which a lumen through which the wire passes is formed and an expansion portion connected to a distal end portion of the drive shaft to the target position of the blood vessel through the guiding catheter; connecting a hub movable in an axial direction together with the drive shaft while rotatably holding the drive shaft and the guiding catheter to a portable operation unit including a drive source that rotates the drive shaft; and integrally moving the drive shaft, the expansion portion, the guiding catheter, and the operation unit in the axial direction to crush an object in the blood vessel by the expansion portion.

In the treatment method according to (15) described above, since the drive shaft, the expansion portion, the guiding catheter, and the operation unit are integrally moved to crush the object in the blood vessel by the expansion portion, the rotating drive shaft and/or the expansion portion can be prevented from interfering with the guiding catheter to damage the guiding catheter.

(16) The treatment method according to (15) described above may further include disconnecting the hub and the guiding catheter from the operation unit after the object in the blood vessel is crushed by the expansion portion. As a result, after the object in the blood vessel is crushed by the expansion portion, the guiding catheter can be operated independently of the operation unit, the hub, the drive shaft, and the expansion portion.

(17) The treatment method according to (16) described above may further include sucking, by the guiding catheter, the object in the blood vessel crushed by the expansion portion after disconnecting the hub and the guiding catheter from the operation unit. As a result, after the object in the blood vessel is crushed by the expansion portion, the guiding catheter can be disposed at a position desired for suction, so that the crushed object in the blood vessel can be effectively sucked and removed.

BRIEF DESCRIPTION OF THE DRAWINGS

FIG. 1 is a plan view illustrating a device support, a medical device, and an introducer sheath according to an embodiment.

FIGS. 2A and 2B are views illustrating the device support in an extended state, where FIG. 2A is a plan view and FIG. 2B is a longitudinal sectional view.

FIG. 3A is a plan view and FIG. 3B is a longitudinal sectional view.

FIG. 4A illustrates a first modification, and FIG. 4B illustrates a second modification.

FIGS. 5A to 5D are plan views illustrating an operation state of the device support, in which FIG. 5A illustrates a state in which the device support is being attached to the medical device, FIG. 5B illustrates a state in which the medical device to which the device support is attached in a contracted state is inserted into a sheath, FIG. 5C illustrates a state in which the device support is extended to cover an outer tube between a sheath hub and a hub and a drive shaft with the device support, and FIG. 5D illustrates a state in which the medical device is moved in a distal end direction to contract the device support.

FIG. 6 is a plan view illustrating a state in which the hub and the operation unit are moved forward and backward in the axial direction with respect to the sheath hub.

FIGS. 9A and 9B are transverse sectional views illustrating a fifth modification of the device support, in which FIG. 9A illustrates a state in which a slit of a support portion is closed by a lid portion, and FIG. 9B illustrates a state in which the slit of the support portion is opened.

FIGS. 10A and 10B are plan views illustrating a sixth modification of the device support, in which FIG. 10A illustrates a state in which an expandable portion is contracted, and FIG. 10B illustrates a state in which the expandable portion is expanded.

DETAILED DESCRIPTION

Figure 3A:
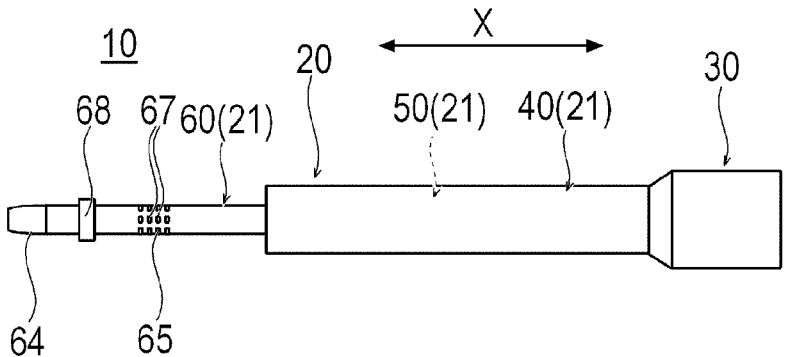
FIGS. 3A and 3B are views illustrating the device support in a contracted state, where

Set forth below with reference to the accompanying drawings is a detailed description of embodiments of a device support used for supporting a medical device to be inserted into a body lumen, a medical device, and a treatment method. Note that dimensional ratios in the drawings may be exaggerated and different from actual ratios for convenience of description.

A device support 10 according to the present embodiment supports a medical device 100 that is inserted into a blood vessel and performs a treatment of crushing thrombus, plaque, calcified lesion, or the like outside the body, and is used to suppress the medical device 100 from being sharply bent outside the body and being damaged. In the present specification, a side of the device support 10 toward the blood vessel will be referred to as a "distal end side", and a side away from the blood vessel will be referred to as a "proximal end side". Furthermore, a direction in which the device support 10 extends in a long direction is referred to as an axial direction X. Furthermore, the medical device 100, the device support 10, and a wire device 300 to be described later form one medical device. In the present specification, crushing means breaking an object by a structure, and a shape of the structure, a breaking method, a degree of breaking, a range of breaking, a shape of the broken object, and the like are not limited.

Figure 1:
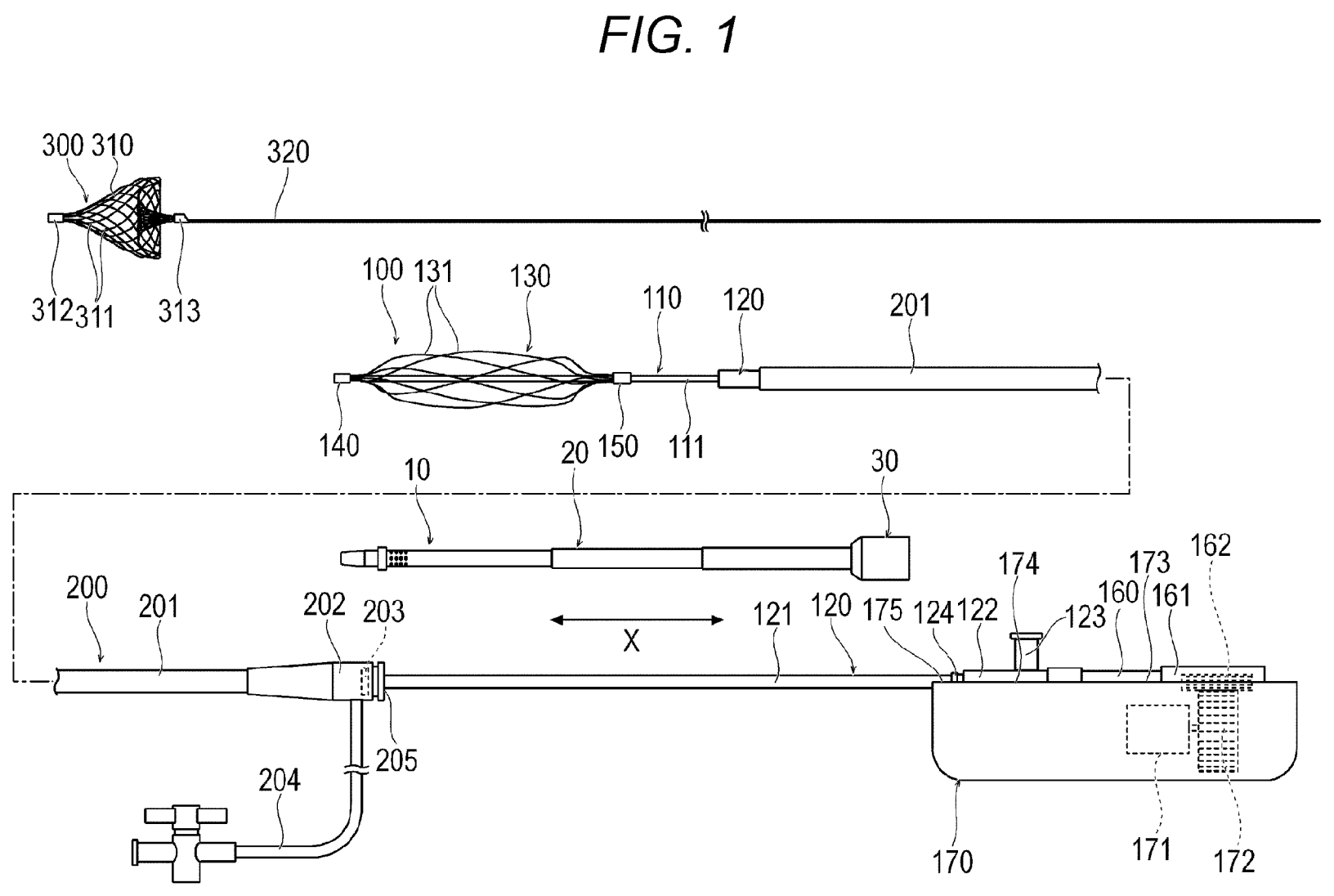

First, the medical device 100 will be described. As illustrated in FIG. 1, the medical device 100 includes a shaft portion 110, an outer tube 120, an expansion portion 130, a fixing portion 140, a slide portion 150, a hub 160, and an operation unit 170.

The shaft portion 110 is a portion that transmits a rotational force to the expansion portion 130. The shaft portion 110 includes a drive shaft 111.

The drive shaft 111 is an elongated tubular body that transmits the rotational force from a proximal end portion to a distal end portion. The proximal end portion of the drive shaft 111 passes through the hub 160. The proximal end portion of the drive shaft 111 is rotatably disposed on the hub 160.

The drive shaft 111 has flexibility so as to be movable in the blood vessel. Moreover, the drive shaft 111 preferably has relatively high torsional rigidity so that the rotational force can be transmitted from the proximal end portion to the distal end portion. The drive shaft 111 can be, for example, a metal tubular body in which a spiral slit is formed. A constituent material of the drive shaft 111 can be preferably, for example, stainless steel or the like.

The fixing portion 140 is a ring-shaped member that fixes the expansion portion 130 to the shaft portion 110. The fixing portion 140 is fixed to an outer peripheral surface of the distal end of the drive shaft 111. Moreover, the fixing portion 140 is fixed to the distal end of the expansion portion 130.

The slide portion 150 is a ring-shaped member provided on the outer peripheral surface of the drive shaft 111 so as to be slidable in the axial direction X on the proximal end side of the fixing portion 140. The slide portion 150 is fixed to the proximal end of the expansion portion 130.

The expansion portion 130 is a member that expands in the biological lumen and crushes an object such as thrombus by rotating. The expansion portion 130 is provided at a distal end portion of the shaft portion 110. The expansion portion 130 and the drive shaft 111 have a lumen into which a wire 320 or a guide wire of the wire device 300 described later can be inserted. The expansion portion 130 includes a plurality of wire rods 131. Each of the wire rods 131 is three-dimensionally curved. A distal end of each wire rod 131 is fixed to the fixing portion 140. A proximal end of each wire rod 131 is fixed to the slide portion 150. The fixing positions of the wire rods 131 with respect to the fixing portion 140 and the slide portion 150 are arranged in the circumferential direction. Furthermore, the curved substantially central portions of the respective wire rods 131 are arranged in a circumferential direction at positions spaced apart outward in a radial direction from the shaft portion 110. As a result, the expansion portion 130 has a relatively uniform expansion in the circumferential direction as a whole. The expansion portion 130 expands in the radial direction in a natural state where no external force acts. When the shaft portion 110 rotates, the expansion portion 130 also rotates accordingly, and can crush thrombus in the blood vessel or stir the crushed thrombus. The expansion portion 130 is contracted in the radial direction by receiving a force so that both ends in the axial direction X are separated. Alternatively, the expansion portion 130 is contracted in the radial direction by receiving a force from the outside to the inside in the radial direction.

The wire rod 131 is desirably made of a material having shape memory property so as to be elastically largely deformable. The constituent material of the wire rod 131 can be preferably, for example, a shape memory alloy to which a shape memory effect or superelasticity is imparted by heat treatment, stainless steel, or the like. As the shape memory alloy, a Ni—Ti-based alloy, a Cu—Al—Ni-based alloy, a Cu—Zn—Al-based alloy, a combination of a Ni—Ti-based alloy, a Cu—Al—Ni-based alloy, and a Cu—Zn—Al-based alloy, or the like is suitable.

The outer tube 120 is a catheter (guiding catheter) having a guiding function used to accommodate and guide the medical device 100 and the wire device 300 to a target position. The outer tube 120 may be a general-purpose guiding catheter. The outer tube 120 includes a tubular outer tube main body 121 that rotatably accommodates the drive shaft 111, and an outer tube hub 122 connected to a proximal end portion of the outer tube main body 121. The outer tube main body 121 has flexibility so as to be movable in the blood vessel. The outer tube hub 122 can be connected to the operation unit 170 and can be detached from the operation unit 170. The outer tube hub 122 may be connectable to the hub 160. A suction force may be applied to the outer tube 120 from the proximal end side. In this case, the inner cavity of the outer tube main body 121 communicates with the suction port 123 provided in the outer tube hub 122. The suction port 123 can be connected to, for example, a syringe, a pump, or the like that generates suction force. As a result, the outer tube 120 can suck the thrombus crushed by the expansion portion 130 from the opening on the distal end side through the gap between the outer tube 120 and the drive shaft 111 and release the thrombus to the outside through the suction port 123. In a state where the outer tube hub 122 is connected to the operation unit 170, the distal end of the outer tube main body 121 is positioned on the proximal end side with respect to the expansion portion 130. In a state where the outer tube hub 122 is detached from the operation unit 170, the outer tube 120 moves in the distal end direction with respect to the drive shaft 11, and the expansion portion 130 can be contracted and accommodated by the outer tube main body 121.

The hub 160 is a member gripped and operated by the operator. The hub 160 can include a housing 161 and a first gear 162 fixed to the drive shaft 111. The hub 160 rotatably holds the proximal end portion of the drive shaft 111 and is movable in the axial direction X together with the drive shaft 111.

The housing 161 is passed through the shaft portion 110, and the proximal end of the outer tube 120 is fixed. A part of the first gear 162 is disposed inside the housing 161, and a part of the first gear 162 is exposed to the outside from the housing 161.

The operation unit 170 is a portion that rotationally drives the shaft portion 110. The operation unit 170 is a portable type (portable) that can be lifted and operated by an operator (user). The operation unit 170 includes a drive source 171 such as a motor, a second gear 172 rotated by the drive source 171, a first connection portion 173 to which the hub 160 can be connected, and a second connection portion 174 to which the outer tube hub 122 can be connected. The first connection portion 173 has a recess conforming to the shape of the hub 160. Therefore, the hub 160 fitted and connected to the first connection portion 173 is restricted from moving in the axial direction X with respect to the operation unit 170. The second connection portion 174 has a recess conforming to the shape of the outer tube hub 122. Therefore, the outer tube hub 122 fitted and connected to the second connection portion 174 is restricted from moving in the axial direction X with respect to the operation unit 170. When the first connection portion 173 is connected to the hub 160, the second gear 172 meshes with the first gear 162. As a result, the shaft portion 110 can be rotated by rotating the drive source 171. The drive source 171 can reciprocate in the rotation direction. The drive source 171 is not limited to reciprocating and may rotate in one direction. The operation unit 170 may have a third connection portion 175 to which a proximal end portion (for example, a proximal end connection portion 30 to be described later) of the device support 10 is fitted. The third connection portion 175 has a recessed portion conforming to the shape of the proximal end connection portion 30. Therefore, the proximal end connection portion 30 fitted and connected to the third connection portion 175 is restricted from moving in the axial direction X with respect to the operation unit 170.

The medical device 100 is introduced into the blood vessel through the sheath 200. The sheath 200 can be, for example, an introducer sheath that is percutaneously inserted into a blood vessel to form an access path to the blood vessel and includes a hemostasis valve. The sheath 200 which is an introducer sheath has a known structure and includes a sheath tube 201 which is an elongated tubular body, a sheath hub 202 fixed to a proximal end portion of the sheath tube 201, a valve body 203 disposed in the sheath hub 202, and a side port 204 communicating with a lumen of the sheath hub 202. Furthermore, the sheath into which the medical device 100 is inserted may be a guiding catheter.

Next, the wire device 300 will be described. The wire device 300 is a device having an elongated wire 320. In the present embodiment, an indwelling unit 310 as a filter indwelled in a blood vessel and the wire 320 extending from the indwelling unit 310 to the outside of the body are provided. The wire 320 enables the indwelling unit 310 indwelled in the body lumen to be collected, and also has a function as a guide wire that guides another device (for example, the medical device 100) to a target position. The wire device 300 may be configured by only a wire, for example, a guide wire.

The indwelling unit 310 is a filter that collects an object such as thrombus crushed by the medical device 100 and flowing together with blood. The indwelling unit 310 includes a plurality of flexibly deformable linear bodies 311 braided in a net shape to form a cylindrical body, a distal end side connection portion 312, and a proximal end side connection portion 313 connected to the wire 320. The indwelling unit 310 is not limited to a filter as long as it can be indwelled in the biological lumen, and may be, for example, a balloon or a stent-like member.

The distal end side connection portion 312 fixes the distal ends of the plurality of linear bodies 311. The proximal end side connection portion 313 fixes the proximal ends of the plurality of linear bodies 311 and the distal ends of the wires 320.

In a natural state in which no external force acts, the indwelling unit 310 is turned back in the axial direction by its own elastic force (restoring force) of the linear body 311. When the indwelling unit 310 is turned back, the proximal end side connection portion 313 and the distal end side connection portion 312 approach each other. In the folded state, the indwelling unit 310 has a concave shape opened toward the proximal end side to form a space for collecting thrombus or the like.

When accommodated in the outer tube 120, the indwelling unit 310 is elastically deformed to be in a contracted state having a small outer diameter. Note that the form of the indwelling portion is not particularly limited.

Next, the device support 10 according to the present embodiment will be described.

As illustrated in FIGS. 2A, 2B, 3A and 3B, the device support 10 includes an expandable portion 20. The expandable portion 20 is an elongated member extending from a distal end to a proximal end and is expandable/contractible in the axial direction X, and a proximal end connection portion 30 that is disposed at the proximal end of the expandable portion 20 and is connectable to the outer tube 120 or the operation unit 170.

The expandable portion 20 has a plurality of support portions 21 in which support holes 28 penetrating in the axial direction X are formed. In the present embodiment, the plurality of support portions 21 are the first support portion 40 (first tubular body), the second support portion 50 (second tubular body), and the third support portion 60 (third tubular body). Note that, in the present embodiment, the number of the support portions 21 is 3, but may be 2 or 4 or more. The first support portion 40 is a tubular member connected to the proximal end connection portion 30. The first support portion 40 is formed with a first support hole 41 formed with a constant inner diameter and a first restriction portion 42 disposed on the distal end side of the first support hole 41 and protruding inward in the radial direction. The first restriction portion 42 restricts the movement exceeding a predetermined length in the distal direction of the second support portion 50 with respect to the first support portion 40 to prevent the second support portion 50 from falling off (or separating) from the first support portion 40.

The second support portion 50 is a tubular member having an outer peripheral surface slidable with respect to the inner peripheral surface of the first support portion 40 inside the first support portion 40. The second support portion 50 is formed with a second support hole 51 formed with a constant inner diameter, a second restriction portion 52 disposed on the distal end side of the second support hole 51 and protruding inward in the radial direction, and a second convex portion 53 disposed on the proximal end side of the outer peripheral surface and protruding outward in the radial direction. When the second support portion 50 moves in the distal end direction with respect to the first support portion 40, the second convex portion 53 abuts on the first restriction portion 42 of the first support portion 40, and the movement of the second support portion 50 in the distal end direction is restricted. The second restriction portion 52 restricts the movement of the third support portion 60 in the distal direction beyond a predetermined length with respect to the second support portion 50 to prevent the third support portion 60 from falling off (or separating) from the second support portion 50.

The third support portion 60 is a tubular member having an outer peripheral surface slidable with respect to the inner peripheral surface of the second support portion 50 inside the second support portion 50. The third support portion 60 is formed with a third support hole 61 formed with a constant inner diameter and a third convex portion 63 disposed on the proximal end side of the outer peripheral surface and protruding outward in the radial direction. When the third support portion 60 moves in the distal end direction with respect to the second support portion 50, the third convex portion 63 abuts on the second restriction portion 52 of the second support portion 50, and the movement of the third support portion 60 in the distal end direction is restricted. Furthermore, the third support portion 60 which is the support portion 21 on the most distal end side includes a distal end connection portion 64 arranged at the most distal end, a flexible portion 65 arranged on the proximal end side of the distal end connection portion 64, and an insertion restriction portion 68 arranged on the proximal end side of the distal end connection portion 64 and on the distal end side of the flexible portion 65.

The distal end connection portion 64 is a cylindrical portion in which a distal end through-hole 66 penetrating in the axial direction X is formed. The outer peripheral surface of the distal end connection portion 64 is formed in a tapered shape. At least a part (for example, a distal end portion) of the outer peripheral surface of the distal end connection portion 64 has an outer diameter tapered toward the distal end so as to form a convex curved surface in the cross section where the axial center is located. Therefore, the distal end connection portion 64 can be rather smoothly inserted into the sheath hub 202 and the valve body 203 of the sheath 200, and damage to the sheath hub 202 and the valve body 203 can be suppressed. The frictional resistance between the distal end connection portion 64 and the valve body 203 in a state where the distal end connection portion 64 is inserted into the valve body 203 is larger than the frictional resistance between the first support portion 40 and the second support portion 50 and larger than the frictional resistance between the second support portion 50 and the third support portion 60.

Figure 4A:
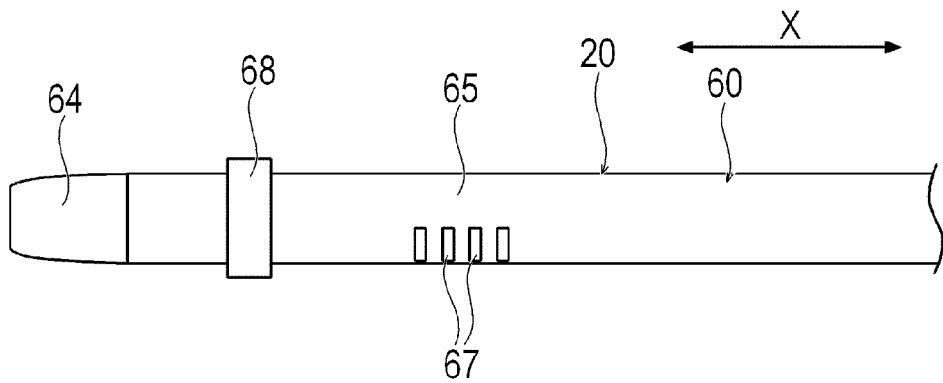
FIGS. 4A and 4B are plan views illustrating a modification of the device support, where

The flexible portion 65 is a portion having partially low flexural rigidity in the axial direction X of the third support portion 60. The flexible portion 65 is formed on the proximal end side with respect to the distal end connection portion 64 and on the distal end side with respect to the range that can be accommodated in the second support portion 50. The structure of the flexible portion 65 is not particularly limited but is formed to have a plurality of opening portions 67 formed to be long in the circumferential direction of the third support portion 60, for example. The opening portion 67 penetrates from the outer peripheral surface to the inner peripheral surface of the third support portion 60. At least one opening portion 67 is arranged in the circumferential direction of the third support portion 60, and at least one opening portion 67 is arranged in the axial direction X of the third support portion 60. When the plurality of opening portions 67 are evenly arranged in the circumferential direction, the flexible portion 65 is rather easily bent in substantially all directions. Furthermore, in the case that the opening portion 67 is disposed only in a part of the third support portion 60 in the circumferential direction as in the first modification in FIG. 4A, the flexible portion 65 is rather easily bent only in the predetermined direction. The opening portion 67 as described above is effective in a case where the bending direction of the third support portion 60 is determined and it is desirable not to bend in other directions.

Figure 4B:
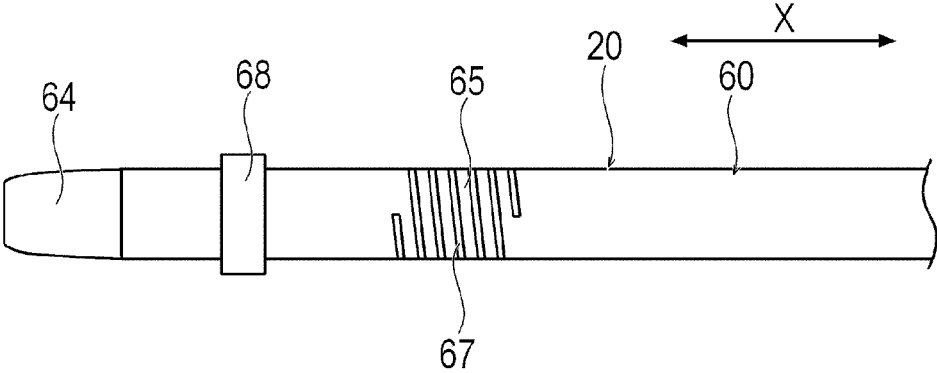

Furthermore, the opening portion 67 of the flexible portion 65 may have a spiral shape as in a second modification illustrated in FIG. 4B.

The insertion restriction portion 68 is a member that suppresses the position of the distal end connection portion 64 where the distal end portion of the third support portion 60 enters the sheath hub 202 of the sheath 200 or the valve body 203 from moving to the distal end side from an appropriate position due to the movement of the medical device 100 in the distal end direction. The insertion restriction portion 68 is formed so as to protrude radially outward from the outer peripheral surface of the third support portion 60. The insertion restriction portion 68 can be, for example, a ring-shaped protruding portion formed over 360 degrees on the outer peripheral surface of the third support portion 60 but may be a protruding portion of less than 360 degrees. The insertion restriction portion 68 abuts on the valve body 203 of the sheath 200 or the outer surface 205 on the proximal end side of the lid holding the valve body 203, thereby preventing the position of the distal end connection portion 64 from moving to the distal end side from an appropriate position. Alternatively, the insertion restriction portion 68 may not have a protruding shape and may be a region where abrasive blasting or the like is performed on the outer peripheral surface of the third support portion 60 so as to increase the friction coefficient.

As illustrated in FIGS. 2A, 2B, 3A, and 3B, the proximal end connection portion 30 is a tubular member to which the proximal end of the first support portion 40 is fixed, and a proximal end through-hole 31 penetrating in the axial direction X is formed so as to communicate with the first support hole 41. An abutment portion 32 against which the proximal end of the second support portion 50 and the proximal end of the third support portion 60 abut is formed in the proximal end through-hole 31 of the proximal end connection portion 30. The abutment portion 32 prevents the second support portion 50 and the third support portion 60 from moving to the proximal end side of the proximal end connection portion 30. Furthermore, the proximal end connection portion 30 is formed with a connection concave portion 33 that can be detachably connected to the connection convex portion 124 of the outer tube hub 122. Note that the connection structure between the proximal end connection portion 30 and the outer tube hub 122 is not particularly limited as long as it can be detachably connected. In the present embodiment, the proximal end connection portion 30 is connected to the distal end portion of the outer tube hub 122, but may be connected so as to be substantially at the same position as the outer tube hub 122 in the axial direction X. Furthermore, the proximal end connection portion 30 may be connected to the outer tube main body 121 in the vicinity of the outer tube hub 122. Furthermore, the proximal end connection portion 30 may be connected to the third connection portion 175 of the operation unit 170.

The support portion 21 (first support portion 40, second support portion 50, and third support portion 60) is preferably formed of a material having relatively high rigidity so as to suppress bending of the drive shaft 111 and the outer tube 120 of the medical device 100, and can be formed of, for example, metal such as stainless steel or resin having high rigidity classified as an engineering plastic. In particular, the support portion 21 is preferably made of metal because it can be formed thin while having high rigidity. The material of the support portion 21 is preferably formed of a material having higher rigidity (Young's modulus) than the outer tube 120 to be supported.

The proximal end connection portion 30 is preferably formed of a material having a certain degree of rigidity, and can be formed of, for example, a resin such as polyether ether ketone (PEEK).

Next, a case where the function of the device support 10 according to the embodiment is applied to the medical device 100 will be described as an example.

Figure 3B:
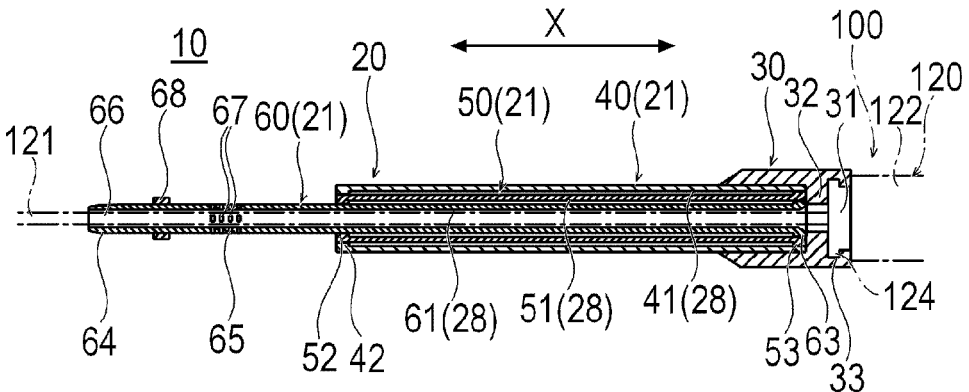

First, as illustrated in FIGS. 3A and 3B, the device support 10 in a contracted state in the axial direction X is prepared. In the device support 10 in the contracted state, the proximal end of the second support portion 50 and the proximal end of the third support portion 60 are in contact with the abutment portion 32 of the proximal end connection portion 30. At this time, the position of the distal end of the second support portion 50 substantially coincides with the position of the distal end of the first support portion 40 in the axial direction X. Furthermore, the position of the distal end of third support portion 60 is located on the distal end side with respect to the position of the distal end of first support portion 40 and the position of the distal end of second support portion 50. Moreover, in the axial direction X, the positions of the distal end connection portion 64 and the flexible portion 65 of the third support portion 60 are located on the distal end side with respect to the position of the distal end of the first support portion 40 and the position of the distal end of the second support portion 50.

Figure 5A:
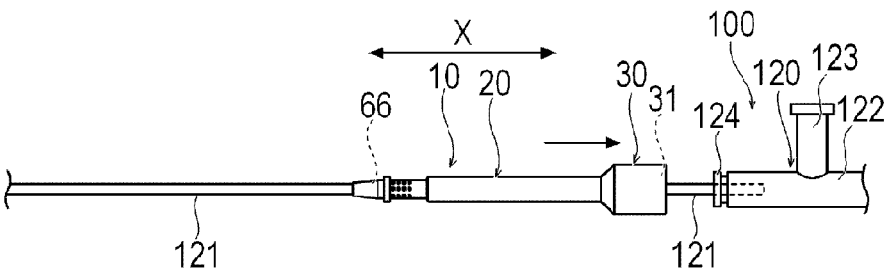

Next, as illustrated in FIGS. 3B and 5A, the operator inserts the outer tube 120 of the medical device 100 into the proximal end through-hole 31 of the proximal end connection portion 30 of the device support 10, and passes the outer tube 120 through the proximal end through-hole 31, the third support hole 61, and the distal end through-hole 66 of the device support 10.

Figure 5B:
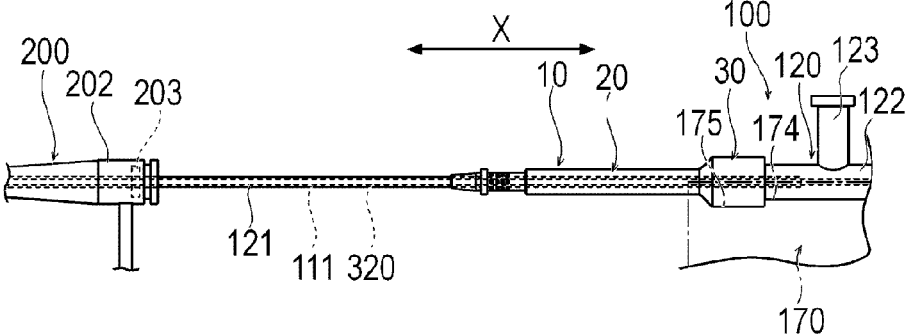

Next, as illustrated in FIG. 5B, the operator engages the connection concave portion 33 of the proximal end connection portion 30 of the device support 10 with the connection convex portion 124 of the outer tube hub 122 of the medical device 100. As a result, the proximal end connection portion 30 of the device support 10 is connected to the outer tube 120 of the medical device 100.

Next, the operator conveys the wire device 300 to a target position in the blood vessel by the outer tube 120. The operator percutaneously inserts the wire device 300 accommodated in the outer tube 120 by contracting the indwelling unit 310 into the proximal end opening of the sheath hub 202 of the sheath 200 inserted into the blood vessel. Next, the surgeon releases the indwelling unit 310 from the outer tube 120 at a position beyond a lesion such as thrombus (a position downstream of the lesion). When released from the outer tube 120, the indwelling unit 310 expands so as to generate a pressing force against the blood vessel wall by its own expansion force and is indwelled in the blood vessel wall.

Next, the operator conveys the medical device 100 to a target position in the blood vessel by the outer tube 120. The operator inserts the medical device 100 accommodated in the outer tube main body 121 by contracting the expansion portion 130 into the blood vessel along the wire 320 extending from the indwelling unit 310 to the outside of the body and causes the medical device to reach the vicinity of the lesion. The wire 320 slides through the lumen of the medical device 100. Next, the operator moves the outer tube main body 121 to the proximal end side with respect to the drive shaft 111 and discharges the expansion portion 130 fixed to the distal end portion of the drive shaft 111 from the outer tube main body 121. When released from the outer tube main body 121, the expansion portion 130 is restored to its original shape by its own elastic force.

Figures 2A, 2B:
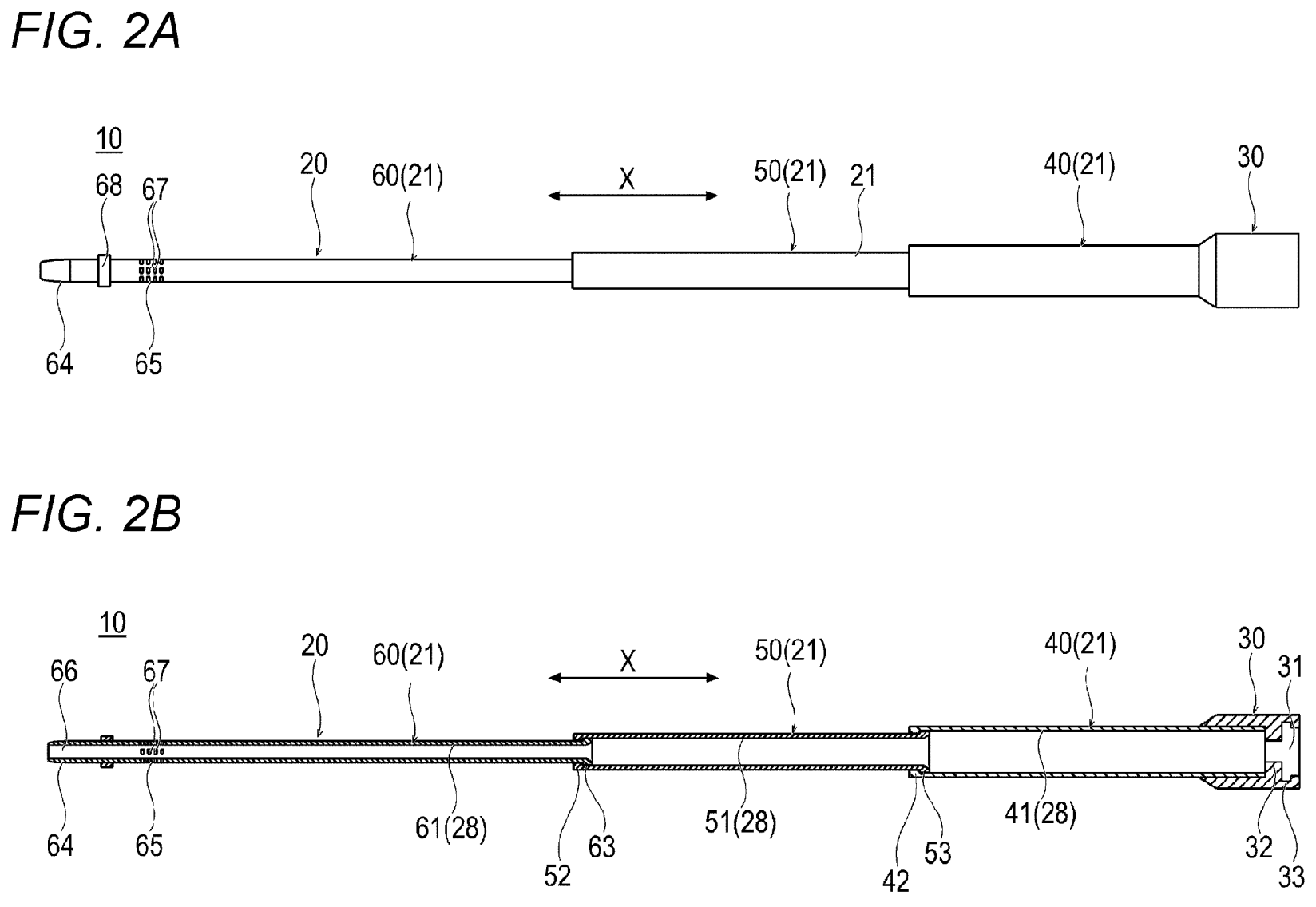
Figure 5C:
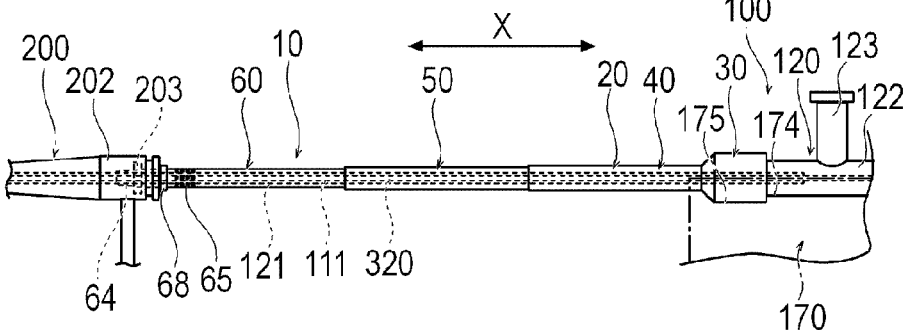

Next, the operator connects the hub 160 to the first connection portion 173 of the operation unit 170 and connects the outer tube hub 122 to the second connection portion 174. When the medical device 100 is connected to the first connection portion 173 of the operation unit 170, the second gear 172 of the operation unit 170 meshes with the first gear 162 of the medical device 100. Thus, the drive shaft 111 can be rotated by rotating the drive source 171. The drive source 171 can reciprocate in the rotation direction. Note that the drive source 171 is not limited to reciprocating and may rotate in one direction. Next, as illustrated in FIG. 5C, the operator grips the third support portion 60 of the device support 10 and moves the third support portion 60 in the distal end direction with respect to the proximal end connection portion 30. In the device support 10, since the frictional resistance between the third support portion 60 and the second support portion 50 is larger than the frictional resistance between the second support portion 50 and the first support portion 40, the second support portion 50 is drawn out (or extends) in the distal end direction with respect to the first support portion 40. As illustrated in FIG. 2B, when the second convex portion 53 of the second support portion 50 abuts the first restriction portion 42 of the first support portion 40, the second support portion 50 is prevented from further moving in the distal end direction with respect to the first support portion 40. When the second support portion 50 moves in the distal direction with respect to the first support portion 40, the third support portion 60 moves in the distal direction together with the second support portion 50.

After the second convex portion 53 of the second support portion 50 abuts the first restriction portion 42 of the first support portion 40, the operator further moves the third support portion 60 in the distal end direction with respect to the proximal end connection portion 30. At this time, since the second support portion 50 is prevented from further moving in the distal direction, the third support portion 60 is pulled out in the distal direction with respect to the second support portion 50. In this manner, the plurality of support portions 21 appropriately move according to the length to be extended, which allows the device support 10 to extend to a desired length.

As illustrated in FIG. 5C, the operator extends the device support 10 until the distal end connection portion 64 is inserted into the valve body 203 of the sheath hub 202. Since the outer peripheral surface of the distal end connection portion 64 is tapered, the distal end connection portion is rather smoothly inserted into the valve body 203, and damage to the valve body 203 can be suppressed. Since the distal end connection portion 64 is inserted to the valve body 203 of the sheath hub 202, the distal end portion of the expandable portion 20 tends to be parallel to the sheath hub 202.

When the distal end connection portion 64 enters the proximal end opening of the sheath hub 202, the elongated outer tube 120 of the medical device 100 exposed on the proximal end side of the proximal end of the sheath 200 is covered and supported by the device support 10.

Figure 5D:
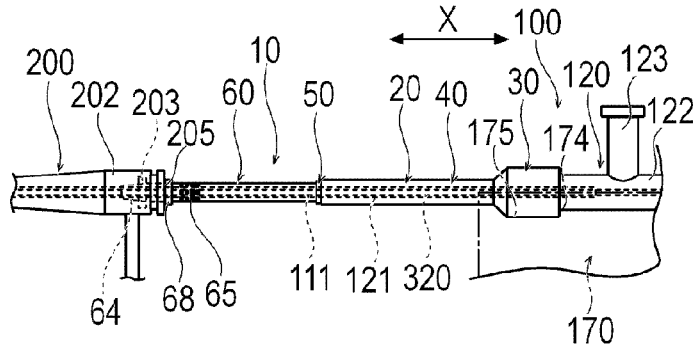

In the device support 10, the frictional resistance between the support portions 21 on the proximal end side is smaller than the frictional resistance between the support portions 21 on the distal end side. Therefore, as illustrated in FIG. 5D, when the slidable support portions 21 on the most proximal end side slide first and the support portions 21 cannot slide any more, the other slidable support portions 21 on the most proximal end side slide. Therefore, when the device support 10 extends and contracts, the support portions 21 on the most distal end side (in the present embodiment, the third support portion 60 and the second support portion 50) slide last. Therefore, it is possible to prevent the distal end connection portion 64 and the flexible portion 65 arranged in the third support portion 60 which is the support portion 21 on the most distal end side from being accommodated in the second support portion 50 and the first support portion 40 on the proximal end side.

The device support 10 has high bending rigidity and is difficult to bend except for the flexible portion 65. Therefore, in the device support 10 between the sheath hub 202 and the outer tube hub 122, a portion excluding the flexible portion 65 is linear, and only the flexible portion 65 is curved, as necessary. For this reason, even if it is difficult to dispose the hub 160 and the operation unit 170 straight on the extension line in the proximal direction from the proximal end portion of the sheath 200, it is possible to support the outer tube 120 and the drive shaft 111 so as not to bend as much as possible by the device support 10 by bending only the flexible portion 65 while making most of the device support 10 linear. In particular, since the proximal end portion of the sheath 200 extend from the blood vessel to the outside of the body is extended in an inclined manner with respect to the skin, when the outer tube hub 122, the hub 160, and the operation unit 170 are arranged on the extension line in the proximal direction from the proximal end portion of the sheath 200, the positions of the outer tube hub 122, the hub 160, and the operation unit 170 tend to be relatively high from the operating table. Therefore, by providing the flexible portion 65 in the device support 10, the outer tube hub 122, the hub 160, and the operation unit 170 can be arranged at appropriate positions where a procedure such as an operating table can be rather easily performed.

Figure 6:
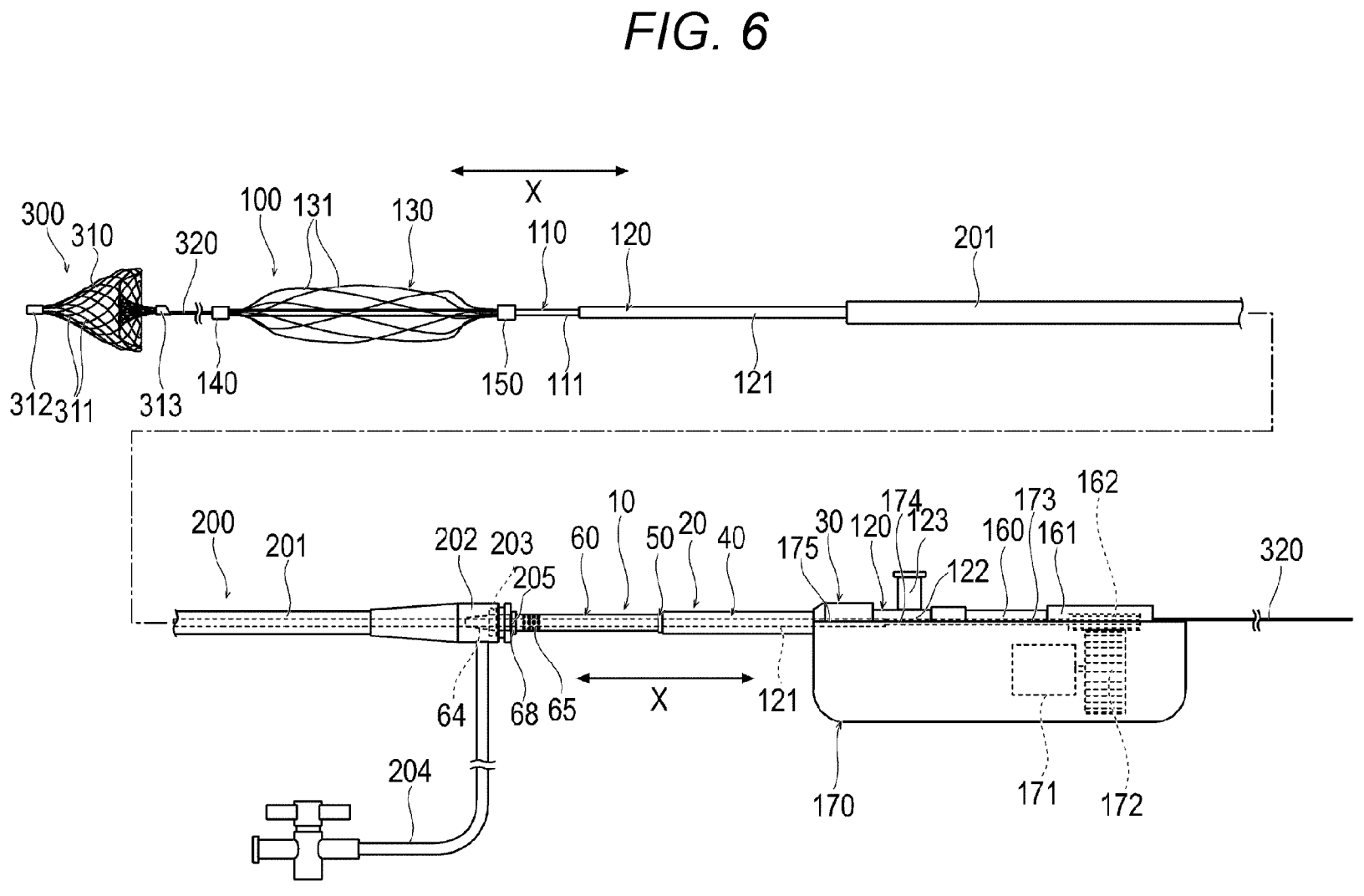

Next, as illustrated in FIG. 6, when the operator actuates the drive source 171, the first gear 162 meshed with the second gear 172 rotated by the drive source 171 rotates, and the drive shaft 111 and the expansion portion 130 rotate. The drive source 171 can reciprocate in the rotation direction. Note that the drive source 171 is not limited to reciprocating and may rotate in one direction.

The operator can alternately move the outer tube hub 122, the hub 160, and the operation unit 170 in the distal direction and the proximal direction with respect to the sheath hub 202 to change the pushing amount of the outer tube 120 and the drive shaft 111, thereby alternately moving the rotating expansion portion 130 in the distal direction and the proximal direction in the blood vessel. Accordingly, the expansion portion 130 can effectively cut thrombus. At this time, since the outer tube hub 122, the hub 160, and the operation unit 170 integrally move in the axial direction X, the outer tube 120 and the drive shaft 111 integrally move in the axial direction X, the length of the drive shaft 111 exposed from the distal end opening of the outer tube 120 to the distal end side does not change. Therefore, even if the expansion portion 130 comes into contact with the thrombus, the drive shaft 111 is difficult to bend without changing the range not supported by the outer tube 120, so that it is difficult to transmit the force in the distal direction, and it is possible to suppress deterioration of the ability to cut the thrombus. Furthermore, since the positions of the expansion portion 130 and the distal end opening of the outer tube main body 121 do not change, the rotating expansion portion 130 and the outer tube main body 121 do not interfere with each other (do not contact each other), and damage to the outer tube main body 121 can be suppressed. The cut thrombus flows together with the blood and is collected so as to be filtered to the indwelling unit 310 which is a filter.

When the operator alternately moves the outer tube hub 122, the hub 160, and the operation unit 170 in the distal end direction and the proximal end direction with respect to the sheath hub 202 in order to alternately advance and retreat the expansion portion 130 in the axial direction X, the distance between the sheath hub 202 and the outer tube hub 122 changes. The outer tube main body 121 and the drive shaft 111 between the sheath hub 202 and the outer tube hub 122 are thin and thus rather easily bent. However, since the distance between the sheath hub 202 and the outer tube hub 122 changes, it is difficult to cover the outer tube main body 121 and the drive shaft 111 in advance with a metal tube or the like having a certain length and high rigidity. If a rigid metal tube having a certain length is placed over the outer tube main body 121 and the drive shaft 111 between the sheath hub 202 and the outer tube hub 122, the metal tube becomes an obstacle, and it becomes difficult to push the outer tube main body 121 and the drive shaft 111 in the distal direction with respect to the sheath 200. However, in the present embodiment, the outer tube main body 121 and the drive shaft 111 between the sheath hub 202 and the outer tube hub 122 are supported by the device support 10 that is hardly bent and can expand and contract in the axial direction X. The device support 10 that is difficult to bend can suppress bending of the outer tube main body 121 and the drive shaft 111 between the sheath hub 202 and the outer tube hub 122. Therefore, when the operator operates the operation unit 170, the outer tube hub 122, or the hub 160 to move in the distal end direction and the proximal end direction, the outer tube main body 121 and the drive shaft 111 can be moved in the axial direction X while bending of the outer tube main body 121 and the drive shaft 111 between the sheath hub 202 and the outer tube hub 122 is suppressed. Therefore, the device support 10 can rather smoothly maintain the rotation of the drive shaft 111 and can suppress damage to the outer tube main body 121 and the drive shaft 111.

Furthermore, the frictional resistance between the distal end connection portion 64 and the valve body 203 in a state where the distal end connection portion 64 is inserted into the valve body 203 is larger than the frictional resistance between the first support portion 40 and the second support portion 50 and larger than the frictional resistance between the second support portion 50 and the third support portion 60. Therefore, when the hub 160 and the operation unit 170 are alternately moved in the distal end direction and the proximal end direction with respect to the sheath hub 202, the distal end connection portion 64 moves together with the valve body 203 without being pulled out from the valve body 203, so that the device support 10 can automatically expand and contract following the movement.

After crushing the thrombus by the expansion portion 130, the operator stops the drive source 171 and stops the rotation of the shaft portion 110. Next, the operator detaches the hub 160 from the first connection portion 173 of the operation unit 170 and detaches the outer tube hub 122 from the second connection portion 174. Next, the operator moves the hub 160 to the proximal end side relative to the outer tube hub 122 to accommodate and contract the expansion portion 130 in the outer tube main body 121. Thereafter, the operator moves the medical device 100 to the proximal end side with respect to the outer tube 120 and removes the medical device 100 from the outer tube 120. Next, the operator pulls out the distal end connection portion 64 of the device support 10 from the sheath hub 202 and contracts the device support 10 in the axial direction X. Note that the operator may maintain a state in which the distal end connection portion 64 of the device support 10 is connected to the sheath hub 202.

Next, the operator places the distal end of the outer tube main body 121 near the position where the thrombus is collected in the indwelling unit 310. At this time, a syringe or the like is connected to the suction port 123 of the outer tube 120 to apply suction force. As a result, the thrombus collected by the indwelling unit 310 can be suctioned and removed from the opening at the distal end of the outer tube main body 121. At this time, since the outer tube 120 can be detached from the operation unit 170 and moved independently, it can be disposed at a position desired for aspirating thrombus. Therefore, the outer tube 120 can effectively suction and remove the thrombus in the crushed blood vessel.

After completing the aspiration of thrombus by the outer tube 120, the operator pushes the outer tube 120 in the distal end direction while pulling the wire 320 in the proximal end direction and accommodates the outer tube main body 121 while contracting the indwelling unit 310. Thereafter, the operator removes the outer tube 120, the device support 10, and the wire device 300 from the introducer sheath 200, and further removes the introducer sheath 200 from the blood vessel. At this time, the device support 10 may be extended or contracted in the axial direction X.

As described above, the device support 10 according to the present embodiment is a device support 10 that is insertable into the sheath 200 and supports the medical device 100 including the rotatable drive shaft 111 extending from the distal end to the proximal end and the operation unit 170 accommodating the drive source 171 connected to the drive shaft 111. The device support includes a plurality of tubular bodies accommodating the drive shaft 111. Among the plurality of tubular bodies, the tubular body disposed on the most proximal end side has the proximal end connection portion 30 connectable to the operation unit 170 at the proximal end of the tubular body. The plurality of tubular bodies includes at least the first tubular body (first support portion 40) and the second tubular body (second support portion 50) having an outer diameter smaller than the inner diameter of the first tubular body. The first tubular body and the second tubular body are relatively movable. As a result, in the device support 10, while the medical device 100 moves in the axial direction X with respect to the sheath 200 into which the drive shaft 111 and the outer tube 120 of the medical device 100 is inserted, the plurality of tubular bodies can suppress the curvature of the rotatable drive shaft 111 of the medical device 100, smoothly maintain the rotation of the drive shaft 111, and can suppress the damage of the drive shaft 111. Furthermore, the plurality of tubular bodies are relatively movable such that the device support 10 inserts only the distal end portion of the device support 10 into the sheath 200 while the medical device 100 is inserted into the sheath 200 up to the vicinity of the proximal end portion. Therefore, the device support 10 can suppress the curvature of the rotatable drive shaft 111 of the medical device 100 to smoothly maintain the rotation of the drive shaft 111 and can suppress the sheath 200 from being deformed due to excessive insertion of the device support 10 into the sheath 200. Therefore, the device support 10 can suppress damage to the drive shaft 111 and other elongated devices used together with the drive shaft 111 such as the sheath 200.

The first tubular body (first support portion 40) is nested and disposed coaxially with the second tubular body (second support portion 50). As a result, the first tubular body and the second tubular body can expand and contract in the axial direction, and can cover the medical device 100 with the lumen of the first tubular body and the second tubular body to effectively suppress the curvature of the drive shaft 111 and the outer tube 120 of the medical device 100.

Furthermore, a device support 10 according to the present embodiment is a device support 10 that supports a medical device 100 including a rotatable drive shaft 111 extending from a distal end to a proximal end, an outer tube 120 extending from a hub 160 in a distal end direction and rotatably accommodating the drive shaft 111, and an operation unit 170 accommodating a drive source 171 connected to the drive shaft 111. The device support 10 can include: an expandable portion 20 formed to be long from the distal end to the proximal end and expandable/contractible in an axial direction X which is an elongated direction; and a proximal end connection portion 30 arranged at the proximal end of the expandable portion 20 and connectable to the outer tube 120 and/or the operation unit 170. The expandable portion 20 includes at least two support portions 21 in which a support hole 28 penetrating in the axial direction X is formed. The at least two support portions 21 are disposed side by side by side in the axial direction X. As a result, the device support 10 can suppress the curvature of the rotatable drive shaft 111 of the medical device 100 and the outer tube 120 that rotatably accommodates the drive shaft 111 while the medical device 100 moves in the axial direction X with respect to the sheath 200 into which the drive shaft 111 and the outer tube 120 of the medical device 100 are inserted by the expandable portion 20 having the support portion 21, and can smoothly maintain the rotation of the drive shaft 111. Furthermore, the expandable portion 20 of the device support 10 is stretchable such that the device support 10 inserts only the distal end portion of the device support 10 into the sheath 200 while the medical device 100 is inserted into the sheath 200 up to the vicinity of the proximal end portion. Therefore, the device support 10 can suppress the curvature of the rotatable drive shaft 111 of the medical device 100 and the outer tube 120 that rotatably accommodates the drive shaft 111 to smoothly maintain the rotation of the drive shaft 111 and can suppress the sheath 200 from being deformed due to excessive insertion of the device support 10 into the sheath 200. Therefore, the device support 10 can suppress damage to the drive shaft 111 and damage to other long devices used together with the drive shaft 111 such as the sheath 200 and the outer tube 120.

The at least two support portions 21 are a plurality of coaxially arranged nested tubular bodies, and the support holes 28 are formed in the lumen of the tubular body. As a result, the support portion 21 can expand and contract in the axial direction X, and the medical device 100 can be reliably covered by the support hole 28 of the inner cavity, and the curvature of the drive shaft 111 and the outer tube 120 of the medical device 100 can be effectively suppressed.

The expandable portion 20 has a tubular distal end connection portion 64 in which a distal end through-hole 66 penetrating in the axial direction X is formed at the distal end portion, and the outer diameter of the outer peripheral surface of the distal end connection portion 64 decreases in a tapered shape toward the distal end so as to form a convex curved surface in the cross section where the axial center is located. As a result, the distal end connection portion 64 of the device support 10 can be inserted into the proximal end opening of the sheath 200, and the device support 10 can be rather smoothly connected to the sheath 200 without damaging the sheath 200.

Among the plurality of tubular bodies, the tubular body (third support portion 60) disposed on the most distal end side may have a distal end connection portion 64 that is disposed at the distal end portion of the tubular body and is insertable into the sheath 200, and an insertion restriction portion 68 that is disposed on the proximal end side of the distal end connection portion 64 and restricts insertion of the tubular body into the sheath 200. As a result, it is possible to prevent the tubular body disposed on the most distal end side from moving to the distal end side from an appropriate position.

The insertion restriction portion 68 may protrude radially outward from the outer peripheral surface of the tubular body disposed on the most distal end side among the plurality of tubular bodies. As a result, the insertion restriction portion 68 of the tubular body disposed on the most distal end side can help prevent the tubular body from moving to the distal end side from an appropriate position.

In the expandable portion 20, a flexible portion 65 having low flexural rigidity may be partially formed in the axial direction X. As a result, a portion of the device support 10 excluding the flexible portion 65 becomes linear, and only the flexible portion 65 can be curved, as necessary. Therefore, even in a case where it is difficult to dispose the operation unit 170 straight on the extension line in the proximal direction from the proximal end portion of the sheath 200, it is possible to support the outer tube 120 and the drive shaft 111 so as not to bend more than necessary by making most of the device support 10 linear and bending only the flexible portion 65.

Among the plurality of tubular bodies, the tubular body (third support portion 60) disposed on the most distal end side is formed with the flexible portion 65 having partially low bending rigidity in the axial direction X. As a result, a portion of the device support 10 excluding the flexible portion 65 becomes linear, and only the flexible portion 65 can be curved, as necessary. Therefore, even in a case where it is difficult to dispose the operation unit 170 straight on the extension line in the proximal direction from the proximal end portion of the sheath 200, it is possible to support the outer tube 120 and the drive shaft 111 so as not to bend more than necessary by making most of the device support 10 linear and bending only the flexible portion 65.

The flexible portion 65 may be an opening portion 67 penetrating from the outer peripheral surface extending in the circumferential direction of the tubular body (third support portion 60) disposed on the most distal end side to the inner peripheral surface. Thus, the flexible portion 65 can be rather easily formed on the tubular body.

By moving the operation unit 170 to which the drive shaft 111, the outer tube 120, and the device support 10 are connected to the distal end side in a state where the distal end portion of the device support 10 is fixed to the sheath 200, the distal end portion of the device support 10 fixed to the sheath 200 may not move, and the drive shaft 111 and the outer tube 120 may move to the distal end side. As a result, the device support 10 can help suppress the curvature of the drive shaft 111 and the outer tube 120 that move with the movement of the operation unit 170 and can rather smoothly maintain the rotation of the drive shaft 111.

Furthermore, the medical device 100 in the present embodiment is a medical device 100 including a rotatable drive shaft 111 extending from a distal end to a proximal end, an operation unit 170 that accommodates a drive source 171 connectable to the drive shaft 111, and an outer tube 120 that rotatably accommodates the drive shaft 111, in which the operation unit 170 includes a third connection portion 175 (connection portion) connectable to the outer tube 120. As a result, since the outer tube 120 can be connected to the operation unit 170 in the medical device 100, the outer tube 120 can be connected to the operation unit 170 to integrally move the drive shaft 111 and the outer tube 120 when the drive shaft 111 is rotated. For this reason, it is possible to prevent the outer tube 120 from being damaged by interference (for example, contact between the expansion portion 130 and the distal end of the outer tube 120) of the rotating drive shaft 111 and/or the expansion portion 130 rotated by the drive shaft 111 with the outer tube 120.

The outer tube 120 has a suction port 123 communicating with a lumen of the outer tube 120. As a result, the suction force received from the suction port 123 is applied to the inner cavity of the outer tube 120, and an object in the body can be suctioned and removed by the outer tube 120.

The medical device further includes a device support 10 that is formed to be elongated from the distal end to the proximal end and includes an expandable portion 20 that can expand and contract in an axial direction that is a long direction and a proximal end connection portion 30 disposed at the proximal end of the expandable portion 20, and the operation unit 170 can connect the proximal end connection portion 30 of the device support 10. As a result, since the proximal end connection portion 30 of the device support 10 can be moved together with the operation unit 170, operability can be improved.

In a state where the operation unit 170, the outer tube 120, and the device support 10 are connected, the distal end of the outer tube 120 and the distal end of the device support 10 are relatively movable in the axial direction X, which allows the expandable portion 20 of the device support 10 to expand and contract such that the device support 10 inserts only the distal portion of the device support 10 into the sheath 200 while the drive shaft 111 and the outer tube 120 are inserted into the sheath 200.

The expandable portion 20 of the device support 10 has at least two support portions 21 in which the support holes 28 penetrating in the axial direction X are formed, and the at least two support portions 21 are disposed side by side in the axial direction X. As a result, the expandable portion 20 can accommodate and reliably support the long drive shaft 111 and the outer tube 120 in the support hole 28 while being expandable and contractible.

In the treatment method in the present embodiment, the user (operator) conveys the wire device 300 including the wire 320 to a target position of the blood vessel through the guiding catheter (outer tube 120). Next, the user conveys the rotatable drive shaft 111 having a lumen through which the wire 320 passes and the expansion portion 130 connected to the distal end portion of the drive shaft 111 to a target position of the blood vessel via the guiding catheter. Thereafter, while the user rotatably holds the drive shaft 111, the hub 160 movable in the axial direction X together with the drive shaft 111 and the guiding catheter are connected to the portable operation unit 170 including the drive source 171 that rotates the drive shaft 111, and the drive shaft 111, the expansion portion 130, the guiding catheter, and the operation unit 170 are integrally moved in the axial direction X to crush the object in the blood vessel by the expansion portion 130. Accordingly, in the present treatment method, since the drive shaft 111, the expansion portion 130, the guiding catheter, and the operation unit 170 are integrally moved to crush the object in the blood vessel by the expansion portion 130, it is possible to suppress the guiding catheter from being damaged due to the interference of the rotating drive shaft 111 and/or the expansion portion 130 with the guiding catheter. Note that the wire device 300 may have the indwelling unit 310 or may not have the indwelling unit 310. The wire device 300 may be formed of only a wire, for example, a guide wire.

In the above treatment method, the guiding catheter (outer tube 120) may be disconnected from the operation unit 170 after the object in the blood vessel is crushed by the expansion portion 130. As a result, after the object in the blood vessel is crushed by the expansion portion 130, the guiding catheter can be operated independently of the operation unit 170, the hub 160, the drive shaft 111, and the expansion portion 130.

In the above treatment method, after the hub 160 and the guiding catheter (outer tube 120) are disconnected from the operation unit 170, an object in the blood vessel crushed by the expansion portion 130 may be suctioned by the guiding catheter. As a result, after the object in the blood vessel is crushed by the expansion portion 130, the guiding catheter can be disposed at a position desired for suction, so that the crushed object in the blood vessel can be effectively suctioned and removed. At this time, after the user removes the drive shaft 111 from the guiding catheter, the user aspirates thrombus. The user can also aspirate thrombus without removing the drive shaft 111 from the guiding catheter.

Note that the present disclosure is not limited to the embodiment described above, and various modifications may be made by those skilled in the art within the technical idea of the present disclosure. For example, the medical device supported by the support device 10 is not limited to a device that removes thrombus as long as it is a device having a rotating shaft. Therefore, the medical device to which the support device 10 can be applied may be an atherectomy device for removing a lesion or an imaging catheter having functions of intravascular ultrasound (IVUS), optical coherence tomography (OCT), or optical frequency domain imaging (OFDI).

Figure 7:
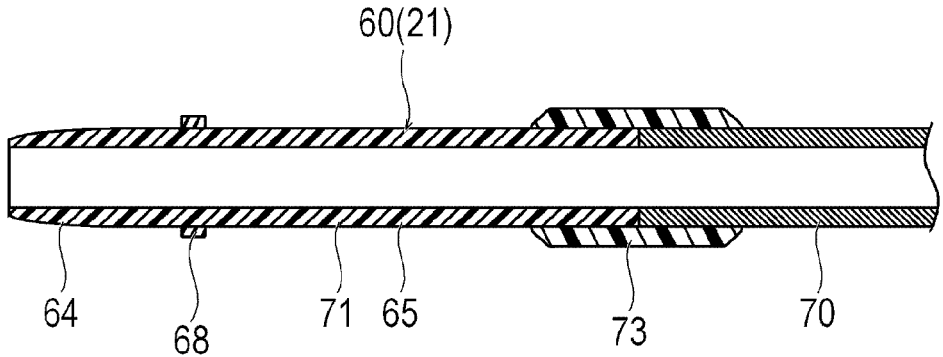
FIG. 7 is a longitudinal sectional view illustrating a third modification of the device support.

Furthermore, as in the third modification illustrated in FIG. 7, the third support portion 60 which is the support portion 21 on the most distal end side may include a high rigidity member 70 having high flexural rigidity on the proximal end side, a low rigidity member 71 having low flexural rigidity on the distal end side, and a kink protector 73 that covers the joint portion between the high rigidity member and the low rigidity member to suppress kink. The low rigidity member 71 forms the flexible portion 65 and the distal end connection portion 64. The high rigidity member 70 can be formed of, for example, a metal material, and the low rigidity member 71 can be formed of, for example, a resin material. The kink protector 73 is disposed on the distal end side of the range that can be accommodated in the second support portion 50. The kink protector 73 can be made of, for example, synthetic rubber or natural rubber. In this case, since the flexible portion 65 can obtain flexibility due to the characteristics of the material, the opening portion 67 or the groove for enhancing the flexibility may not be formed. Furthermore, since the distal end connection portion 64 is flexible, it is possible to suppress damage to the sheath hub 202 and the valve body 203 to be connected.

Figure 8:
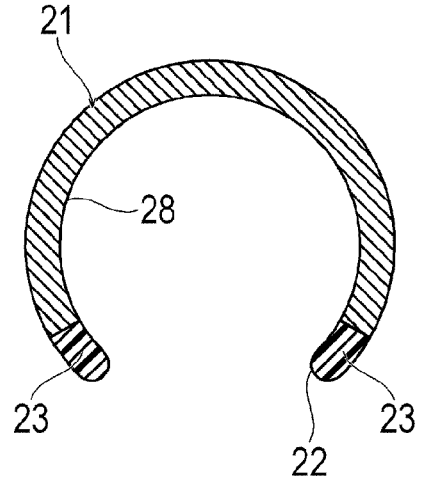
FIG. 8 is a transverse cross-sectional view illustrating a fourth modification of the device support.

Furthermore, as in a fourth modification illustrated in FIG. 8, a slit 22 extending from the distal end to the proximal end may be formed in all the support portions 21 (first support portion 40, second support portion 50, and third support portion 60) and the proximal end connection portion 30. The edge portion 23 of the slit 22 can be, for example, formed of a flexible material such as resin in order to suppress damage to the sheath 200 and the medical device 100. Each support portion 21 is discontinuous by the slit 22 in the circumferential direction that is the direction surrounding the support hole 28. Furthermore, the proximal end connection portion 30 is discontinuous by the slit 22 in the circumferential direction which is the direction surrounding the proximal end through-hole 31. Thus, the device support 10 can receive the outer tube 120 and the drive shaft 111 into the support hole 28 via the slit 22 from the side intersecting the axial direction X of the support portion 21. Therefore, it is not necessary to cover the medical device 100 with the device support 10 in advance before inserting the medical device 100 into the sheath 200, and workability can be improved. Thus, for example, even with the drive shaft 111 and the outer tube 120 of the medical device 100 inserted into the sheath 200, the device support 10 can be attached to the medical device 100 such that the outer tube 120 and the drive shaft 111 are received in the support hole 28.

Figure 9A:
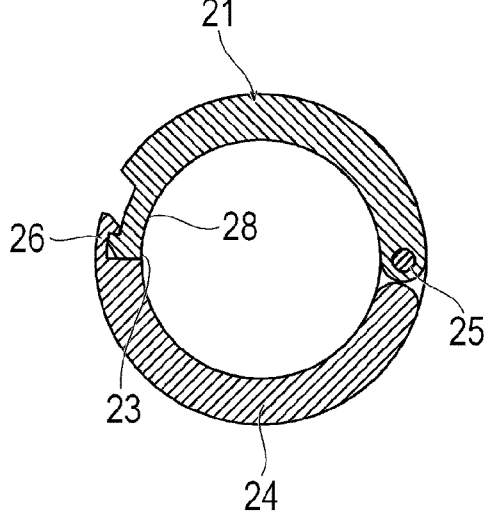
Figure 9B:
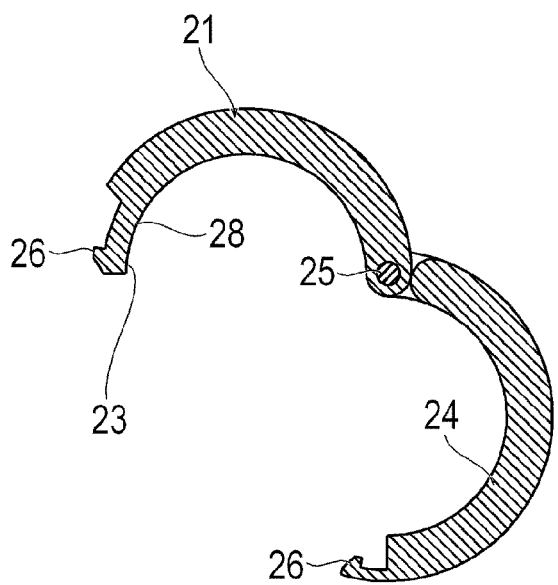

Furthermore, as in a fifth modification illustrated in FIGS. 9A and 9B, all the support portions 21 (first support portion 40, second support portion 50, and third support portion 60) and the proximal end connection portion 30 may be formed with a slit 22 extending from the distal end to the proximal end, and the support portion 21 (first support portion 40, second support portion 50, and third support portion 60) may have a lid portion 24 capable of opening and closing the slit 22. That is, the support portion 21 is formed in a shape obtained by dividing the tubular body into halves. The lid portion 24 is rotatably connected to the vicinity of the slit 22 of the support portion 21 where the slit 22 is formed by a hinge 25 and can be maintained in a closed state by an engagement portion 26. The structure of the engagement portion 26 is not particularly limited, but can be formed by, for example, two hooks that can be engaged and disengaged. Thus, the device support 10 can close the slit 22 by the lid portion 24 after receiving the outer tube 120 and the drive shaft 111 from the slit 22 into the support hole 28. Therefore, the device support 10 can help prevent the outer tube 120 and the drive shaft 111 from separating from the support hole 28 via the slit 22.

Figure 10A:
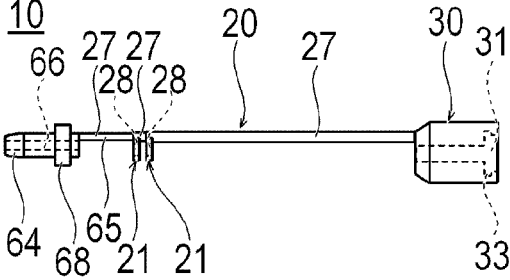
Figure 10B:
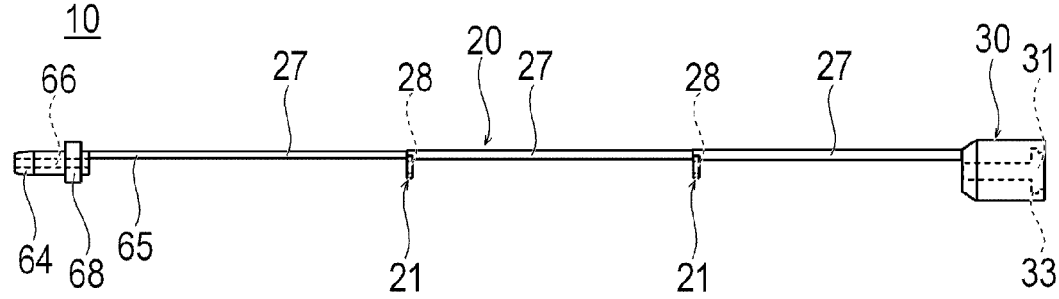

Furthermore, as in a sixth modification illustrated in FIGS. 10A and 10B, the expandable portion 20 may have a plurality of beams 27 arranged slidably in the axial direction X, and the support portion 21 that guides the outer tube 120 and the drive shaft 111 may be fixed to the beams 27 and formed in a ring shape. The beam 27 may be formed of a plurality of nested tubular bodies but may be a linear motion mechanism such as a slide rail since it does not have to include a lumen. As a result, the device support 10 can support the medical device 100 at a plurality of positions in the axial direction X by the plurality of support holes 28 formed in the plurality of ring-shaped support portions 21. Therefore, it is possible to effectively suppress the curvature of the drive shaft 111 and the outer tube 120 of the medical device 100 outside the body. The slit 22 illustrated in FIG. 8 or the lid portion 24 illustrated in FIGS. 9A and 9B may be formed in the ring-shaped support portion 21.

The detailed description above describes embodiments of a device support used for supporting a medical device to be inserted into a body lumen, a medical device, and a treatment method. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A treatment method comprising:
conveying a wire device including a wire through a guiding catheter to a target position of a blood vessel;
conveying a rotatable drive shaft in which a lumen through which the wire passes and an expansion portion connected to a distal end portion of the drive shaft to the target position of the blood vessel through the guiding catheter;
connecting a hub movable in an axial direction together with the drive shaft while rotatably holding the drive shaft and the guiding catheter to a portable operation unit including a drive source that rotates the drive shaft; and
integrally moving the drive shaft, the expansion portion, the guiding catheter, and the operation unit in the axial direction to crush an object in the blood vessel by the expansion portion.

2. The treatment method according to claim 1, further comprising:
disconnecting the hub and the guiding catheter from the operation unit after the object in the blood vessel is crushed by the expansion portion.

3. The treatment method according to claim 2, further comprising:
suctioning, by the guiding catheter, the object in the blood vessel crushed by the expansion portion after disconnecting the hub and the guiding catheter from the operation unit.

4. The treatment method according to claim 1, further comprising:
inserting the guiding catheter into a proximal end through-hole of a proximal end connection portion of a device support;
passing the guiding catheter through the proximal end through-hole of the device support, an expandable portion of the device support, and a distal end through-hole of the device support;

connecting the guiding catheter to a proximal end connection portion of the expandable portion of the device support; and expanding or contracting the expandable portion of the device support in an axial direction.

5. The treatment method according to claim 4, wherein the expandable portion includes two or more support portions in which a support hole penetrating in the axial direction is formed, and at least two of the two or more support portions are disposed side by side in the axial direction.

* * * * *